US006660905B1

(12) United States Patent
Kay et al.

(10) Patent No.: US 6,660,905 B1
(45) Date of Patent: Dec. 9, 2003

(54) MICE COMPRISING ENGRAFTED FUNCTIONAL HUMAN HEPATOCYTES

(75) Inventors: Mark A. Kay, Los Altos, CA (US); Kazuo Ohashi, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/614,658

(22) Filed: Jul. 12, 2000

Related U.S. Application Data

(60) Provisional application No. 60/143,897, filed on Jul. 14, 1999.

(51) Int. Cl.[7] .................. A01K 67/00; A01K 67/033; A01K 63/00; C07K 16/00; C12P 21/08
(52) U.S. Cl. .................. 800/8; 424/93.1; 530/388.1; 530/388.15; 530/388.2
(58) Field of Search ................ 800/18, 21, 22, 800/26, 3, 8; 424/93.1; 530/388.1, 388.15, 388.2

(56) References Cited

FOREIGN PATENT DOCUMENTS

| WO | WO 9509235 A | 4/1995 |
|----|--------------|--------|
| WO | WO 9639810 A | 12/1996 |
| WO | WO 9800543 A | 1/1998 |

OTHER PUBLICATIONS

Webster's II; New Riverside University Dictionary, 1984 : 778.*
Romano et.al.; Latest Developments in Gene Transfer Technology: Achievements, Perspectives, and Controversies over Therapeutic Applications, 2000, Stem Cells 18: 19–39.*
Palu et.al.; In pursuit of new developments for gene therapy of human diseases, 1999, Journal of Biotechnology 68: 1–13.*
Saadi et.al.; Immunology of Xenotransplantation, 1998, Life Sciences, vol. 62: 365–387.*
Inverardi et.al.; Cell Transplantation, 1996, Transplantation Biology: Cellular and Molecular Aspects: 679–687.*
Kanazawa et. al.; Prospects for Xenotransplantation of the Liver, 2000, Seminars In Liver Disease vol. 20, No. 4: 511–522.*
Grompe; Mouse Liver Goes Human: A New Tool in Experimental Hepatology, 2001, Hepatology: 1005–1006.*
Miller et. al.; Targeted vectors for gene therapy, 1995, FASEB J. 9: 190–199.*
Deonarain; Ligand–targeted receptor–mediated vectors for gene delivery, 1998, Exp. Opin. Ther. Patents *(1): 53–69.*
Verma et. al.; Gene therapy– promises, problems and prospects, 1997, Nature vol. 389: 239–242.*
Crystal; Transfer of Genes to Humans: Early Lessons and Obstacles to Success, 1995, Science vol. 270: 404–410.*

Adams et. al.; Experimental Manipulation of Human Hepatocytes for Hepatic Gene Therapy . . . Transplantation in SCID Mice, 1992, J. Cell Biochem Suppl.: 57.*
Araki et al. (1989), "Expression and replication of hepatitis B virus genome in transgenic mice." *Proc. Natl. Acad. Sci.*, vol. 86:207–211.
Bishop et al. (1990), "Antiviral Strategies in Chronic Hepatitis B Virus Infection: I. Establishment of an In Vitro System Using the Duck Hepatitis B Virus Model." *Journal of Medical Virology*, vol. 31:82–89.
Cressman et al. (1996), "Liver Failure and Defective Hepatocyte Regeneration in Interleukin–6–Deficient Mice." *Science*, vol. 274:1379–1383.
Fausto et al. (1995), "Role of growth factors and cytokines in hepatic regeneration." *The FASEB Journal*, vol. 9:1527–1536.
Fontaine et al. (1995), "Human Hepatocyte Isolationand Transplantation Into an Athymic Rat, Using Prevascularized Cell Polymer Constructs." *Journal of Pediatric Surgery*, vol. 30(1):56–60.
Guidotti et al. (1995), "High–Level Hepatitis B Virus Replication in Transgenic Mice." *Journal of Virology*, vol. 69(10):6158–6169.
Lampertico et al. (1991), "Development and Application of an in Vitro Model for Screening Anti–hepatitis B Virus Therapeutics." *Hepatology*, vol. 13(3): 422–426.
Rhim et al. (1994), "Replacement of Diseased Mouse Liver by Hepatic Cell Transplantation." *Science*, vol. 263:1149–1152.
Chang et al. (1997) "Agonistic antibodies to c–Met, the HGF receptor, selectively stimulate proliferation vs. migration." *FASEB J.*, vol. 11(3): A523 Abstract.
Elcin et al. (1999) "Xenotransplantation of fetal porcine hepatocytes in rats using a tissue engineering approach." *Artificial Organs*, vol. 23(2):146–152.
Ohashi et al. (2000) "Sustained survival of human hepatocytes in mice: A model for in vivo infection with human hepatitis B and hepatitis delta viruses." *Nature Medicine*, vol. 6(3):327–331.

(List continued on next page.)

*Primary Examiner*—Deborah Crouch
*Assistant Examiner*—Thai-An N. Ton
(74) *Attorney, Agent, or Firm*—Bret E. Field; Bozicevic, Field & Francis

(57) ABSTRACT

Non-human mammalian hosts are provided, comprising functional human hepatocytes. Isolated human hepatocytes or fragments of human hepatic tissue are introduced into the xenogeneic host in conjunction with one or more agent that stimulates human hepatocyte growth factor receptor. The human hepatocytes are maintained in the host by administration of one or more agent that stimulates human hepatocyte growth factor receptor, either continuously (e.g., via an implanted catheter or intravenous apparatus) or in discrete, regular dosages of the agent (e.g., via intravenous injections or oral dosages). The human hepatocytes are able to survive and function in the host animal for a period of at least 5 months.

30 Claims, 6 Drawing Sheets

OTHER PUBLICATIONS

Sanhadji et al. (1992), "Fetal liver cell transplantation in various murine models." *Bone Marrow Transplant*, vol. 9(Suppl. 1):77–82.

Sureau (1993), "In vitro culture systems for hepatitis B and delta viruses." *Arch Virol*, Suppl. 8:3–14.

Taub (1996), "Transcriptional control of liver regeneration." *The FASEB Journal*, vol. 10:413–427.

Webber et al. (1994), "In Vivo Response of Hepatocytes to Growth Factors Requires an Initial Priming Stimulus." *Hepatology*, vol. 19(2):489–497.

Yamada et al. (1998), "Deficient Liver Regenration after Carbon Tetracholride Injury in Mice Lacking Type 1 but Not Type 2 Tumor Necrosis Factor Receptor." *American Journal of Pathology*, vol. 152(6):1577–1589.

* cited by examiner

SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: synthesized oligonucleotide

<400> SEQUENCE: 1
ggagtgtgga ttcgcact

```
<210> SEQ ID NO 2
<211> LENGTH: 18
<212> TYPE: DNA
<213> ORGANISM: Artificial Sequence
<220> FEATURE:
<223> OTHER INFORMATION: synthesized oligonucleotide

<400> SEQUENCE: 2
tgagatcttc tgcgacgc                                             18

<210> SEQ ID NO 3
<211> LENGTH: 30
<212> TYPE: DNA
<213> ORGANISM: Artificial Sequence
<220> FEATURE:
<223> OTHER INFORMATION: synthesized oligonucleotide

<400> SEQUENCE: 3
tagaagaaga actccctcgc ctcgcagacg                                30
```

MICE COMPRISING ENGRAFTED FUNCTIONAL HUMAN HEPATOCYTES

CROSS-REFERENCE

This application claims the benefit of U.S. Provisional Application No. 60/143,897, filed Jul. 14, 1999, which application is incorporated herein by reference.

GOVERNMENT RIGHTS

The United States Government may have certain rights in this application pursuant to Grant NIH AI 41320.

TECHNICAL FIELD

The field of this invention is mammals comprising xenogeneic tissue, and in particular xenogeneic hepatocellular tissue.

BACKGROUND

The liver is a critically important organ for monitoring and adjusting plasma constituents. Hepatocytes are active in controlling levels of blood glucose, lipids and cholesterol, and a number of plasma proteins, including albumin, fibrinogen and prothrombin, and several complement factors. The structure of a liver lobule is that of a hexagon with portal triads at each corner, where each triad contains branches of the hepatic portal vein, hepatic artery and bile duct, so that each hepatocyte is in a close association with the vascular system.

Hepatocytes synthesize triglycerides, cholesterol and phospholipids. Much of the lipid synthesized is then packaged with proteins and released into the circulation as VLDLs, providing a source of fatty acids for all cells. Hepatocytes also synthesize the enzyme essential for formation of cholesterol esters in HDL, remove chylomicron fragments from the circulation, and are an indirect source of LDLs, which are formed in plasma from VLDLs depleted of fatty acids. Balancing the lipoprotein levels and cholesterol content in the circulation has proven to be a critical factor in vascular disease.

Glucose from the blood is stored by hepatocytes in the form of glycogen, which is a major source of glucose for other cells in the body. During meals with high glucose, insulin increases the ability of hepatocytes to synthesize glycogen. As blood glucose drops, glucagon and epinephrine increase the ability of hepatocytes to degrade glycogen. Enzyme deficiencies associated with glycogen deficiencies can result in storage diseases. The liver also has other specialized function other than glucose storage, including: detoxification; synthesis of critical plasma proteins, such as coagulation proteins, alpha-1 antitrypsin, and albumin; amino acid and ammonia metabolism; heme synthesis; and vitamin and cofactor biosynthesis.

Despite its specialized functions, the liver has a unique regenerative capacity. After partial hepatectomy, the liver mass is restored by division of fully differentiated hepatocytes. Even in adults, these cells have a tremendous replicative ability. The existence of liver stem cells remains controversial, but such cells may be active in liver growth after severe injury.

The response of hepatocytes to tissue damage is mediated by several cytokines. Immediately after an injury, hepatocytes undergo a priming phase in which they become competent to enter the cell cycle. This phase is characterized by expression of the proto-oncogenes c-myc and c-jun. The primed cells are then able to respond to cytokines such as epidermal growth factor (EGF), tumor growth factor (TGF-α), Interleukin-6 (IL-6), and hepatocyte growth factor (HGF). TGF-α is synthesized by hepatocytes and acts as an autocrine factor. The in vivo response of hepatocytes to growth factors is discussed in references such as Y. Yamada et al., *Am J Pathol.* 152:1577–89 (1998); D. E. Cressman et al., *Science* 274:1379–83 (1996); R. Taub, *FASEB J.*10:413–27 (1996); N. Fausto et al., *FASEB J.* 9:1527–36 (1995); Webber et al., *Hepatol* 19:489–497 (1994).

Certain viruses such as hepatitis viruses show great specificity for infecting hepatocytes. Several hundred million people worldwide suffer from chronic hepatitis B virus (HBV) or hepatitis C virus infection which greatly increases their risk of developing liver cirrhosis and/or hepatocellular carcinoma (HCC). Medical therapy is generally not curative, and when available, transplanted livers can become re-infected. The only animals that can be infected with human hepatitis B virus (HBV) or human hepatitis C virus (HCV) are humans and chimpanzees, and the major tissue that is productively infected is the liver, although there have been reports of infected stromal cells.

Although in vitro models of hepatitis B and C have been used to study hepatitis virus infection (see e.g., Sureau,*Arch. Virol.*8:3–14 (1993); P. Lampertico et al., *Hepatology* 13:422–6 (1991); and N. Bishop et al.,*J Med Virol.* 31:82–9 (1990), these models are limited as to the study of disease progression. Gene expression in the in vitro models is altered from normal in vivo expression in hepatocytes. Primary hepatocyte cultures are susceptible to infection for only a few days, if at all, and do not produce the characteristic infectious particles. Human hepatitis D virus (HDV) requires envelope proteins produced by HBV, and therefore can only infect cells susceptible to HBV. The need for a good experimental system having cells that are susceptible to productive infection by viruses such as the hepatitis viruses, and other hepatic pathogens, remains.

The field of medicine relies heavily on animal models. These models provide a means of analyzing the effect of viruses and other pathogens, cytokines, environmental factors, hormones, diet, and the like. Without animal models, it is extremely difficult to perform controlled experiments. An animal model having viable human tissue provides numerous advantages over other systems such as in vitro cultured tissue. One can investigate the effect of agents on the tissue at various stages in the development of the disease. The interactions of cells, secreted age tissue can also be analyzed. A xenogeneic animal model further provides a means of testing the effect of factors and other agents on cells that are difficult to maintain in culture. Short-lived lymphocyte subsets, neural cells, complex tissues, neutrophils, etc. that cannot easily be grown in culture for extended periods of time may be examined.

In view of the many important functions performed by the liver, it is of substantial interest to develop and provide animal models comprising functional human hepatocytes that remain viable for extended periods of time. An animal model would permit investigation of the function and dysfunction of hepatocytes, the etiology of disease and the effect of pathogens and therapeutic drugs.

Many different approaches for creating an animal model for liver disease using hepatocellular transplantation have been tried over the years. Hepatocytes of the same or similar species can be stably transplanted into the liver via the spleen or portal vasculature and shown to function in a hepatocyte specific manner. While hepatocellular transplantation within the same or related species has been established, see e.g., Rhim et al. *Science* 263:1149–1152 (1994), the creation of a mouse that can persistently harbor functional human hepatocytes and is susceptible to infection with HBV or HCV has not been demonstrated. Previous mouse or rat models show a low rate of persistence of hepatocyte function (K. Sanhadji et al., Bone Marrow *Trans.* 9:77–82 (1992); M. Fontaine et al., *J. Ped. Surgery* 30:56–60 (1995)). Transgenic mice expressing the hepatitis B genome replicates the virus, resulting in viremia, but not a normal course of hepatitis infection (M. J. Araki et al., *Proc Natl Acad Sci USA* 86:207–11(1989); M. B. Guidotti et al.,*J. Virol* 6:6158–69 (1995)). Chimpanzees and other higher primates remain the only species besides humans susceptible to infection with hepatitis B or C viruses.

There is thus a need in the art for animal models that allow the study of human liver dysfunction, e.g., dysfunction caused by pathogenic or parasitic infection or exposure to chemical agents. There is also a need in the art for a system that allows the study of normal human liver development and function.

SUMMARY OF THE INVENTION

Non-human mammalian hosts are provided, comprising functional human hepatocytes. Isolated human hepatocytes or fragments of human hepatic tissue are introduced into the xenogeneic host in conjunction with an agent, e.g., one or more activator that stimulates signaling through the human hepatocyte growth factor receptor (hHGFR). In one embodiment, the human hepatocytes are maintained in the host by administration of one or more agent that stimulates human hepatocyte growth factor receptor, either continuously (e.g., via an implanted catheter or intravenous apparatus) or in discrete, regular dosages of the agent (e.g., via intravenous injections or oral dosages). The human hepatocytes are able to survive and function in the host animal for a period of over 5 months. The chimeric animal has broad applicability in the study of human infectious diseases with hepatocellular tropism, degenerative and metabolic diseases of the human liver, and toxic or carcinogenic agents that target the human liver.

The invention also provides a method for enhancing the transplantation and/or maintenance of the human hepatocytes by the administration of growth factors, angiogenic factors, cytokines, or other agents that further promote the colonization and growth of the human hepatocytes in the mammalian host. In a specific embodiment, the invention provides enhancement of transplantation using a factor, e.g., FGF, that enhances vascularization at the transplantation site.

It is an object of the invention to provide an animal model for hepatitis infections, and particularly HBV, HDV and HCV infection.

It is another object of the invention to provide an animal model for human parasitic infection in which the parasite must pass through a liver phase, e.g., the human malaria parasites *Plasmodium vivax* and *Plasmodium falciparum*.

It is yet another object of the invention to provide an animal model for human disorders involving exposure to chemicals or toxins, such as alcoholic cirrhosis.

It is yet another object of the invention to provide an animal model for studying normal human liver development and function.

It is yet another object of the invention to identify the efficacy of gene therapeutics to human liver cells, e.g. the transfer of genes with vectors specific to human and/or liver cells, or gene therapy to treat viral infections.

It is an advantage of the invention that the effect of agents on human hepatocytes are functional in vivo for an extended period of at least five months or more, and thus can be examined at various stages of development, pathogenic infection, or toxicity.

It is another advantage of the invention that the chimeric animals provide a means of testing the effect of factors and other agents on human hepatocytes, which are difficult to maintain in culture.

It is yet another advantage of the invention that the human hepatocytes in the chimeric animals are in an in vivo setting, and thus associate with other cells specific to an in vivo setting, e.g., short-lived lymphocyte subsets, neural cells, complex tissues, neutrophils, etc. that cannot easily be grown in culture for extended periods of time.

It is yet another advantage that the chimeric animals of the invention may be created in animals with various genetic backgrounds.

These and other objects, advantages, and features of the invention will become apparent to those persons skilled in the art upon reading the details of the chimeric animals as more fully described below.

DETAILED DESCRIPTION OF THE PREFERRED EMBODIMENTS

Figure 1:
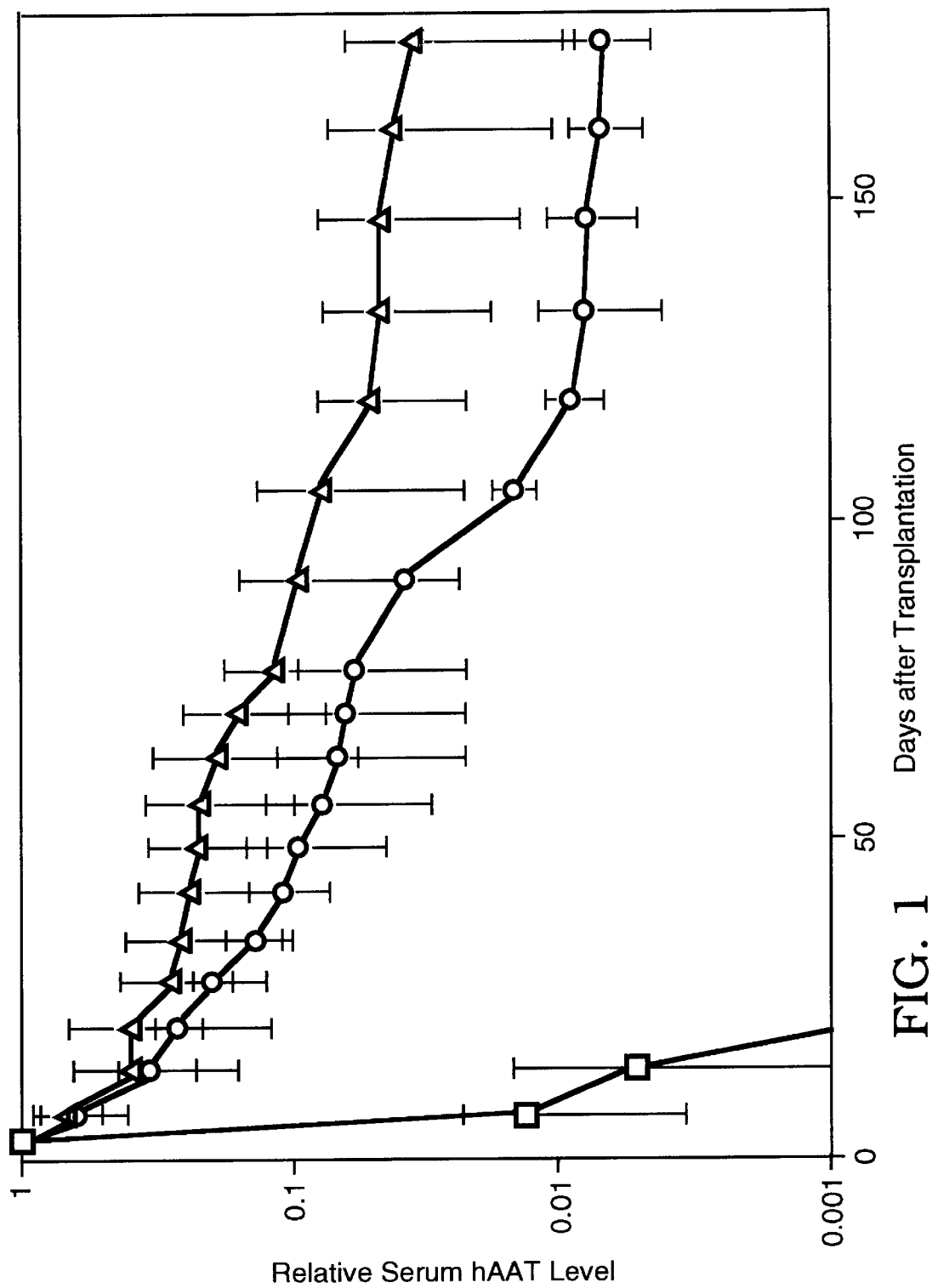
FIG. 1 is a graph showing the persistence of human hepatocytes transplanted in NOD/SCID mice. Human hepatocytes were transplanted into the subcutaneous space (6×106 cells, diamonds; n=8), kidney capsule (4×106 cells, triangles; n=10) or into the liver by intraportal infusion (2×106 cells, squares; n=6). The data are a combined set of three different experiments from different adult hepatocyte donors.

Before the present chimeric animals are described, it is to be understood that this invention is not limited to particular methods and strains described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an animal" includes multiple animals and reference to "the agonist" includes reference to one or more agonist, a plurality and/or combination of such agonists, and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "engraftment" as used herein refers to the establishment of a xenographic transplant in a host organism. Preferably, the engraftment of the invention will be stable after about two weeks, and the engraftment will remain viable for at least five months in the presence of administration of an agent that enhances hHGFR activity and/or signaling.

The term "HGFR activator" and "hHGFR activator" as used herein describe any molecule, e.g., protein or small molecule pharmaceutical, antibody, DNA sequences encoding an hHGFR protein or peptide, and the like, with the capability of promoting signaling through hHGFR. This includes an agonist that binds to and activates hHGFR (e.g., hHGF or an antibody that binds to the extracellular domain of hHGFR), full-length hHGFR protein, a constitutively activated form of hHGFR (e.g., an hHGFR protein with a transmembrane mutation or an hHGFR peptide lacking the extracellular domain), a peptide or small molecule that binds to and activates hHGFR. For purposes of the present invention, the term "hHGFR activator" additionally encompasses DNA sequences encoding a molecule that promotes hHGFR signaling, e.g., an expression vector encoding one or more of these molecules. Such sequences may be in an expression vector that allows production of the protein encoded by the sequences in the hepatocytes.

The term "promotes signaling of the hHGFR" as used herein refers to any activity which increases the signaling through hHGFR, e.g., by binding to and activating hHGFR, by increasing the concentration of hHGFR, by providing a constitutively active form of hHGFR, and the like.

The term "therapeutic agent" as used herein refers to any molecule, e.g., protein or small molecule, pharmaceutical compound, antibody, antisense molecule, ribozyme, and the like, with the ability to treat a human liver condition in vivo. For example, therapeutic agents of the invention include molecules that inhibit, ameliorate, or relieve symptoms associated with viral infection, and in particular HBV, HDV and/or HCV. In another example, therapeutic agents of the invention are used to prevent or cure parasitic infections. In yet another example, therapeutic agents can be used to protect the liver from toxicity or physical damage, or to promote in the recovery from such chemical or physical damage.

The term "vaccine" as used herein refers to any therapeutic agent that inhibits or lessens the infectivity of a virus. The vaccine may be administered in one or more dose prior to potential exposure, at the time of exposure, or after initial exposure to the virus to prevent establishment of infection or to decrease the initial infectivity of the virus.

The term "unit dosage form," as used herein, refers to physically discrete units suitable as unitary dosages for human and animal subjects, each unit containing a predetermined quantity of agents of the present invention calculated in an amount sufficient to produce the desired effect in association with a pharmaceutically acceptable diluent, carrier or vehicle. The specifications for the novel unit dosage forms of the present invention depend on the particular agent employed and the effect to be achieved, and the pharmacodynamics associated with each compound in the host.

By "antibody" is meant an immunoglobulin protein which is capable of binding an antigen. Antibody as used herein is meant to include the entire antibody as well as any antibody fragments (e.g. $F(ab')_2$, Fab', Fab, Fv) capable of binding the epitope, antigen or antigenic fragment of interest.

Antibodies of the invention are immunoreactive or immunospecific for and therefore specifically and selectively bind to an hHGFR protein or a peptide thereof. Antibodies for hHGFR are preferably immunospecific—i.e., not substantially cross-reactive with related materials. Although the term "antibody" encompasses all types of antibodies (e.g., monoclonal) the antibodies of the invention are preferably produced using the phage display methodology described herein.

By "purified antibody" is meant one which is sufficiently free of other proteins, carbohydrates, and lipids with which it is naturally associated. Such an antibody "preferentially binds" to a native hHGFR protein (or an antigenic fragment thereof), i.e., does not substantially recognize and bind to other antigenically-unrelated molecules. A purified antibody of the invention is preferably immunoreactive with and immunospecific for a hHGFR protein of specific species and more preferably immunospecific for native human hHGFR.

By "antigenic fragment" of a hHGFR protein is meant a portion of such a protein which is capable of binding an antibody useful in the methods of the invention.

By "binds specifically" is meant high avidity and/or high affinity binding of an antibody to a specific polypeptide i.e., epitope of a hHGFR protein. Antibody binding to its epitope on this specific polypeptide is preferably stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to native hHGFR in situ with a binding affinity of $10^7$ mole/l or more, preferably $10^8$ mole/liters or more are said to bind specifically to hHGFR. In general, an antibody with a binding affinity of $10^6$ mole/liters or less is not useful in that it will not bind an antigen at a detectable level using conventional methodology currently used.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing the disease from occurring in a subject which may he predisposed to the disease but has not yet been diagnosed as having it;

(b) inhibiting the disease, i.e., arresting its development; or (c) relieving the disease, i.e., causing regression of the disease.

GENERAL ASPECTS OF THE INVENTION

Methods and compositions are provided for the growth of hepatocytes in a mammalian host, particularly a mouse, for extended periods of time. The method comprises implanting isolated human hepatocytes in an appropriate site in a host, in conjunction with administration of an agent that enhances signaling of hHGFR. The chimeric animal provides an easily manipulated experimental model that is useful for studying human hepatic diseases, normal human liver function, liver malignancies, and the like.

The present invention is based on the finding that engrafted primary human hepatocytes transplanted in the presence of a c-Met agonistic antibody, either in a matrix under the kidney capsule or subcutaneously, retained viability for at least 5 months. The animals were found to be susceptible to hepatitis B virus (HBV) infection after its in vivo infusion, as evidenced by a rise in serum hepatitis B surface antigen (HBsAg), HBV DNA viral titers, and immunohistochemical staining for hepatitis B core antigen. The animals were also susceptible to infection by the hepatitis delta virus (HDV), which often co-infects with HBV. This represents the first stable, long-term, reproducible human hepatocyte xenotransplant model and creates an animal model with an opportunity to investigate the entire HBV, HDV and/or HCV life cycles. The animals of the invention may enhance studies of human hepatocyte biology as well as other types of human disease.

CREATION OF CHIMERIC MAMMALIAN HOSTS

Isolation of Human Hepatocytes

Human hepatocytes for transplantation into the host animals are isolated from human liver tissue by any convenient method known in the art. The human hepatocytes may be fresh tissue (e.g., obtained within about 48 hours of death), or freshly frozen tissue (e.g., tissue frozen within about 12 hours of death and maintained at below about −10°), usually at about liquid nitrogen temperature (−195° C.) indefinitely. The tissue will generally be normal, e.g., non-transformed and non-malignant, except in those cases where study of a particular malignancy is desired.

The liver tissue is optionally cultured in vitro prior to storage and/or transplantation. The cells may be manipulated in vitro, e.g. transfect the cells with a vector containing sequences to be expressed in vivo, or to select for more viable cells to increase the success of the transplantation process. Cells cultured for 48 hours have been shown to maintain viability following engraftment into a mammalian host.

The liver tissue can be dissociated mechanically or enzymatically to provide a suspension of single cells, or fragments of intact human hepatic tissue may be used. In a preferred embodiment, the hepatocytes are isolated from donor tissue by routine collagenase perfusion and low-speed centrifugation. See G. S. Ponder, *Proc Natl Acad Sci USA* 88:1217–21 (1991). The suspension may be enriched for hepatic precursors by Ficoll-hypaque density gradient centrifugation, fluorescence activated cell sorting, panning, magnetic bead separation, elutriation within a centrifugal field, or resetting. Generally a suspension of partially purified hepatocytes, usually at least about 50% hepatocytes by number, more usually at least about 80% hepatocytes by number, and preferably at least 90% hepatocytes by number are used for implantation.

The human hepatocyte suspension is preferably transplanted in conjunction with a substance that enhances transplantation, e.g., a suspension that enhances cellular adhesion or provides structure for engraftment, such as MATRIGEL™ (Becton-Dickinson; Franklin Lakes, N.J.). Other similar matrix suspensions may also be used, as will be apparent to one skilled in the art upon reading the present disclosure. The transplant enhancing substance may additionally contain proteins such as extracellular matrix proteins, angiogenic factors, and the like that will enhance engraftment or maintenance of the transplanted hepatocytes. Preferably, such proteins are human, either recombinant or, more preferably, human derived.

Transplantation of Human Hepatocytes into Hosts

Successful engraftment of hepatocytes is enhanced by contact with the host growth factors, nutrients, and other factors required by the human hepatocytes. The human hepatocytes of the present invention are transplanted into a region that will allow proper engraftment, including direct transplantation to the liver, spleen, subcutaneous transplantation, peritoneal space, ommentum, liver parenhyma, etc. In a preferred embodiment, the human hepatocytes are transplanted under the kidney capsule or subcutaneously.

After introduction of the donor hepatocytes, the cells engraft in the site of implantation. The engrafted cells may be either randomly distributed in the host tissue, or grow as discrete acini. The hepatic cells are fully engrafted after about 1 day, and hAAT can be detected in the animal models almost immediately following transplantation. At one day following transplantation, hepatocytes are functional and amenable to in vivo experimentation, e.g. can be successfully infected by HBV, HDV and/or HCV. The transplanted hepatocytes will remain functional for at least about 5 months, or more. Assays for function may include responsiveness to insulin and glucagon, the ability to produce liver specific proteins, e.g., human serum albumin, c-reactive protein in response to IL-6, and the like. The chimeric animal provides an environment for the introduction of a number of agents that are suspected of causing or contributing to hepatic disease, as well as the appropriate antagonists and blocking therapeutic agents.

The animals of the invention may be any non-primate mammals into which human hepatocytes may be introduced and maintained. This includes, but is not limited to, horses, sheep, cows, cats, dogs, rats, hamsters, rabbits, gerbils, guinea pigs, and mice. Preferably, the host animal is from the genus Rodentia, since these mammals are smaller, have faster developmental growth, and are cheaper to feed and maintain. In a preferred embodiment, the host animal is a mouse. Mice for use in producing the chimeric mice of the invention include the strains CB.17, ICR (outbred), C3H, BALB/c, C57131/6, AKR, BA, B10, 129, etc.

In one preferred embodiment, immunocompromised non-human mammalian hosts are used for transplantation of the human hepatocytes. Immunocompromised mammalian hosts suitable for implantation and having the desired immune incapacity exist or can be created, e.g.,by administration of one or more compounds (e.g., cyclosporin)and other methods well known in the art. The immunocompromised host is generally incapable of mounting a full immune response against the xenogeneic tissue or cells. Of particular interest are small mammals, e.g., rabbits, gerbils, hamsters, guinea pigs, etc., particularly murines, e.g., mouse and rat, which are immunocompromised due to a genetic defect which results in an inability to undergo germline DNA rearrangement at the loci encoding immunoglobulins and T-cell antigen receptors.

Presently available hosts include mice that have been genetically engineered by transgenic disruption to lack the recombinase function associated with RAG-1 and/or RAG-2 (e.g., commercially available TIM™ RAG-2 transgenic), to lack Class I and/or Class II MHC antigens (e.g., the commercially available C1D and C2D transgenic strains), or to lack expression of the Bcl-2 proto-oncogene. Of particular interest are mice that have a homozygous mutation at the scid locus, causing a severe combined immunodeficiency which is manifested by a lack of functionally recombined immunoglobulin and T-cell receptor genes. The scid/scid mutation is available or may be bred into a number of different genetic backgrounds, e.g., CB.17, ICR (outbred), C3H, BALB/c, C57B1/6, AKR, BA, B10, 129, etc. Other mice which are useful as recipients are NOD scid/scid; SGB scid/scid, bh/bh; CB.17 scid/hr; NIH-3 bg/nu/xid and META nu/nu. Transgenic mice, rats and pigs are available which lack functional B cells and T cells due to a homozygous disruption in the CD3F- gene. Immunocompromised rats include HsdHan:RNU-rnu; HsdHan:RNU-rnu/+; HsdHan:NZNU-rnu; HsdHan:NZNU-rnu/+; LEW/HanHsd-rnu; LEW/HanHsd-rnu/+; WAG/HanHsd-rnu and WAG/HanHsd-rnu/+.

The host will usually be of an age less than about 25% of the normal lifetime of the host, usually about 1 to 20% of the normal lifetime. Generally, the host will be at least about four weeks old and large enough to manipulate for introduction of the donor tissue at the desired site. For example, mice are usually used at about 4 to 6 weeks of age. Growth of the tissue within the host will vary with the site of transplantation.

The mammalian host will be maintained in conventional ways. Depending on the degree of immunocompromised status of the mammalian host, it may be protected to varying degrees from infection. If the host is severely immunocompromised, an aseptic environment is indicated. For example, it may be desirable to provide prophylactic antibiotics for protection of scid/scid mice from Pneumocystis infection, for example 25–75 mg trimethoprim and 100–300 mg sulfamethoxazole in 5 ml of suspension, given three days each week, or in impregnated food pellets. Alternatively, it may be satisfactory to isolate the potential hosts from other animals in gnotobiotic environments after cesarean derivation. The feeding and maintenance of the chimeric host will for the most part follow gnotobiotic techniques.

Activators Promoting Hepatocyte Transplantation and Maintenance

The ability of hepatocytes to engraft is promoted by administration of a stimulus for factors involved in liver regeneration, and in particular human hepatocyte growth factor (hHGFR). An activator that stimulates hHGFR is administered at the time of transplantation, and then afterwards as appropriate, e.g., a substantially constant level of administration (e.g., by continuous infusion) or a dosage at regular intervals, such as once every two weeks. Exemplary hHGFR activators for stimulating hHGFR signaling include, but are not necessarily limited to, substantially purified hHGF, substantially purified hHGFR, a substantially purified,.constitutively activated form of the hHGFR, an adenovirus expressing hHGF, a small molecule agonist of hHGF. Preferably the hHGFR activator is an antibody that specifically binds to and activates (i.e. acts as an agonist of) hHGFR. Exemplary hHGFR agonists are disclosed in WO 98/00543, which is incorporated herein by reference for the purpose of describing such molecules.

Substantially purified hHGFR protein, and nucleic acids encoding such proteins, may contain modifications that enhance their activity or provide for constituent activation of the receptor molecule. For example, truncated receptor molecules lacking the extracellular domain Mutations in specific regions of transmembrane receptors are known to confer such increases in activation and signaling, and it is well within the skill of one in the art to predict residues for mutating the hHGFR to increase its basal activity and to test such mutated molecules for increased activity using in vitro kinase assays. Exemplary mutations of transmembrane receptors are disclosed in K. Khazaie et al., *Cancer Metastasis Rev.* 12:255–74 (1993).

Of particular use for activating hHGFR signaling in the host animals of the invention is an antibody that recognizes an epitope on the extracellular domain of the hHGFR, e.g., the monoclonal antibody 3D6, which is a murine IgG1 that binds and activates human but not murine c-Met. 3D6 was generated against a recombinant form of the extracellular domain of human c-Met. 3D6 antibodies have been shown to induce tyrosine phosphorylation of c-Met in MDA-MB-435 mammary carcinoma cells and in A549 lung adenocarcinoma cells and results in hepatocyte proliferation of cultured ferret hepatocytes. Other antibodies that may be used in the animals and methods of the invention can be generated and using techniques known in the art. See e.g., Monoclonal Antibodies: A Laboratory Manual, Harlow and Lane eds., Cold Spring Harbor Laboratories, Cold Spring Harbor, N.Y., 1988.

The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycoplipids, polynucleotides or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

In one embodiment of the invention, the hHGFR activator is administered to the host in the form of a nucleic acid, which may be introduced to the host. Preferably, the nucleic acid encodes an hHGFR activator, such as those described above. Alternatively, the nucleic acid may bind to and promote the signaling activity of the hHGFR. Methods of introducing the nucleic acid include viral vectors, e.g., retroviral and adenoviral vectors, mammalian expression systems, and the like. Nucleic acids comprising an hHGFR activator sequence provided herein are generally propagated by placing the molecule in a vector. Viral and non-viral vectors are used, including plasmids. The choice of plasmid will depend on the type of cell in which propagation is desired, e.g., the human hepatocytes or host cells surrounding the engrafted hepatocytes. Certain vectors are useful for amplifying and making large amounts of the encoded protein in cultured cells: Other vectors are suitable for expression in cells in culture. Still other vectors are suitable for transfer and expression in cells in a whole animal or person. The choice of appropriate vector is well within the skill of the art. Many such vectors are available commercially. Methods for preparation of vectors comprising a desired sequence are well known in the art.

Such sequences can be introduced to the animal prior to or following the transplantation procedure or, alternatively, the human hepatocytes may be transfected or infected with the nucleic acids encoding an hHGFR activator prior to transplantation. Such modes of introduction of genetic sequences will be apparent to one skilled in the art following the reading of the disclosure. For example, intramuscular injection of an adenoviral vector expressing hepatocyte growth factor has been shown to facilitates hepatic transduction with a retroviral vector in mice. C. Gao et al. *Hum Gene Ther*. 10:911–22 (1999). In another example, intracellular expression of a cloned antibody fragment, such as an SFV fragment, can be obtained by introduction and expression in hepatocytes or other exogenous tissue. The application WO 98/06855 describes compositions and methods for delivery of nucleic acids to hepatocytes, and is incorporated herein by reference for this purpose.

Other compounds for use in enhancing hHGFR activity and/or signaling may be identified using assays for receptor activation known in the art. See e.g., A. R. Asthagiri et al., *Anal Biochem* 269:342–7 (1999). Compounds of the invention may affect any portion of the pathway involved in the signaling of HGFR, and preferably directly regulate receptor activity. Compounds identified as enhancing HGFR signaling can be used to ensure proper engraftment of human hepatocytes in the methods of the invention.

Candidate hHGFR activators can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological compounds may be subjected to directed or random chemical modifications, such as acylation, alkylation, esterification, amidification, etc. to produce structural analogs.

Other factors that increase proliferation of hepatocytes may also be used to enhance the human hepatocyte engraftment in the chimeric animals of the invention, including but not limited to insulin, epidermal growth factor (EGF), tumor growth factor a (TGF-α), and a wide variety of factors produced by the gut, pancreas and liver. Fibroblast Growth Factor (FGF) in particular has been shown to increase hepatocyte proliferative activity, see WO/9918128, and can serve to act as an angiogenic factor. The factors may be administered singly or as a cocktail. Preferably human factors will be used, although cross-reactive factors from other species may be used in place of human.

Administration of the growth factors may be through any convenient method, e.g., i.v., i.p., through an osmotic pump or sustained release implant, etc. Preferably, the animal host may be stimulated to produce additional growth factors by a partial hepatectomy. Removal of one-third to two-thirds of the host liver provides adequate supplemental hepatocyte growth factors, along with the administered HGF, to allow proper engraftment. These factors may be those previously characterized, as well as chalones, a class of molecules believed to be responsible for liver regeneration. The growth factors produced by partial hepatectomy of the animal host are sufficiently active on human hepatocytes to enhance engraftment.

Determination of Functionality of Engrafted Human Hepatocytes

Functionality of the hepatocytes can be monitored by looking at surrogate markers for hepatocyte activity, including physiologic products of human hepatocytes distinguishable from their murine analogs by immunologic or quantitative criteria, e.g., expression of human serum albumin, or expression of c-reactive protein in response to IL-6, etc. These markers can be used to determine the presence of cells without sacrifice of the recipient. In a preferred embodiment, the functionality of human hepatocytes is monitored by measuring levels of hATT in the serum of the non-human mammalian host, wherein expression of this human protein is indicative of functionality of the engrafted hepatocytes.

Phenotyping of the xenogeneic hepatocytes to verify their origin and stage of developmental progression may be performed by biopsy of the engrafted hepatocytes followed by standard histological methods, e.g., immunohistochemistry, antibody staining or in situ hybridization with RNA and/or DNA probes. HLA markers may be used to distinguish the established xenogeneic organ transplants, and the HLA type can be readily determined by staining with an appropriate antibody directed against any of the alleles of the human HLA locus, including Class I and Class II antigens.

Transplantation of Additional Tissues in the Host

Human tissues other than hepatocytes may optionally be transplanted into the host with the hepatocytes, either in the same general location or in completely different sites in the non-human mammalian host. For example, hematopoietic components may be included, such as stem cells, lymph nodes, embryonic yolk sac, fetal liver, pancreatic tissue, appendix tissue, tonsil tissue and the like, which may serve to provide human lymphoid and granulocytic cells in the case of an immunocompromised host. Sites for introduction of additional tissue will be dictated by the particular needs and growth potential of that tissue, and may include under the spleen capsule, abdominal wall muscle, under the renal capsule, in the anterior chamber of the eye, the peritoneum, the peritoneal lining, brain, subcutaneous, vascular system, spinal cord, membranous sacs or capsules of various tissue, the retroperitoneal space, reproductive organs, ear pinnae, etc.

Introduction of the optional human tissue may be achieved by injection, implantation, or joining blood vessels (and other vessels if necessary) of the donor and host, using intravenous catheters, trocars, and/or surgical incision, or the like. The tissue or cells of interest will generally be normal, e.g., non-transformed and non-malignant tissue or cells. With various organs one may include native surrounding tissue with the organ tissue itself. The surrounding tissue may comprise connective tissue, or portions of blood and lymphatic vessels. In some cases, whole organ grafts may be transplanted by anastomosing donor and host blood vessels, lymphatic vessels, and the like. For the most part, normal cells, tissue, and/or organs may be stably maintained and functional for at least about 3–6 months and frequently for at least about 10 months.

A mixed population of cells in suspension may be enriched for the particular cells of interest. For example, with bone marrow cells, the suspension may be enriched for T cells by Ficoll-hypaque density gradient centrifugation, fluorescence activated cell sorting, panning, magnetic bead separation, elutriation within a centrifugal field, or resetting. In some instances it may be desirable to enrich cells by killing or removing other cells. This may be achieved by employing monoclonal antibodies specific for the undesired cells in the presence of complement or linked to a cytotoxic agent, such as a toxin, e.g., ricin, abrin, diphtheria toxin, a radiolabel, or the like. Immunoaffinity columns may be employed which allow for specific separation of either the desired or undesired cells, depending on the antibodies or fragments thereof used for separation, and the nature of the mixture.

As appropriate, dispersed cells are employed, where the relevant organs are teased apart to yield viable cells in suspension. Cells of particular interest as a secondary implant are human hematopoietic cells, particular T cells, neutrophils, and other granulocytic and myeloid cells. Such cells may be obtained from an immunocompetent human donor. The hematopoietic cells may be mismatched as to HLA type with the hepatocytes, so as to provide a marker for the source, or may be matched as to HLA type in order to provide T cells that recognize antigen presented by the hepatocytes.

USES OF THE CHIMERIC MAMMALIAN HOSTS

The presence of the human hepatocytes in a non-human mammalian host may be used to study the effect of various compounds on the growth, viability, differentiation, maturation, transformation, or the like, of these human cells in a live host. The chimeric host comprising the functional human hepatocytes may be used to study the effect of a variety of conditions (e.g., temperature, electric potential, ionic strength, drugs, transformation, etc.), symptoms or indications of a disease, normal developmental stages, effects of toxic chemicals, effects of physical damage, and the like. In addition, therapeutic agents to counteract pathogens, vaccines to prevent viral infection, and protectants from chemical and/or physical damage may be screened using the chimeric animals of the invention.

Study of Pathogenic Infections

There are a number of pathogens known to cause hepatitis in humans, including hepatic pathogens, e.g., viruses, protozoans and bacteria. The effect of such pathogens of human hepatocellular tissue may be investigated with the subject animals. Viruses of interest include the human hepatitis viruses A, B, C, and E, particularly HBV, HDV and HCV, which cannot be grown in culture. Other hepatic viruses are Epstein-Barr virus, cytomegalovirus, varicella-zoster virus and yellow fever viruses.

The present invention also allows the study of co-infection by multiple viruses. For example, Hepatitis delta virus (HDV) can accompany HBV infections in humans, often exacerbating the course of liver disease. HDV is an enveloped virus, yet it does not make its own envelope proteins, instead using HBsAg provided by a coexisting HBV infection. The animals of the present invention can be used to study the course of infection of HDV and HBV, as the human hepatocytes can be infected with HBV and provide human HBsAg to allow HDV infection.

A pathogen may be wild-type, e.g., clinical isolates, conventional strains, etc.; attenuated strains; or may be genetically engineered to enhance or reduce infectivity, pathogenicity, etc. Such modifications in the genome may include deletion of virulence genes, mutations in coat proteins that alter the host range, change in viral nucleic acid polymerases, alterations in proteins that affect integration into the host genome, etc. Mutations introduced into the pathogen genome are useful to map the functions of various proteins, and to determine which domains are responsible for various aspects of the infection, i.e. in establishing latency, transforming cells, replication, etc.

To study the effects of infection on human cells, a liver implant is inoculated with the pathogen, usually at an infectious level. The effect of the pathogen is determined, in most cases as a function of time. Data may be obtained as to the response of human cells to the pathogen; products which are secreted by infected or involved cells in response to infection, e.g.,. cytokines, interferons, etc.; the viability and growth of the human hepatocytes; and pathogen replication, e.g., release of new infectious particles or cells.

Infection may be achieved by direct injection of the pathogen. Usually, the injection will involve at least about $10^2$ infectious units, preferably from about $10^3$ to $10^5$ infectious units. The viral pathogen may be a clinical isolate, a cloned clinical isolate, a genetically modified isolate, or the like. Alternatively, administration may be via injection of infected cells, where the injected cells will produce infectious pathogens over time. The cells will deliver a dose of at least about $10^2$ infectious units, preferably from about $10^3$ to $10^5$ infectious units.

Infection of hepatocytes is also an essential feature of certain parasitic infections. Infection of the animals of the invention with these parasites will allow the study of the parasitic infection on human hepatocytes, as well as provide a means for testing the effect and efficacy on anti-parasitic drugs For example, malaria is caused by species of the Plasmodium genus. Four species are known to cause malaria: *P. falciparum*, malignant tertian malaria (the most dangerous and most common world-wide); *P. vivax*, benign tertian malaria (most common human malaria in temperate regions); *P. malariae*, or quartan malaria; and P. Ovalle, or Ovalle malaria. Plasmodium species are sporozoan obligate intracellular parasites of liver and red blood cells. All Plasmodium species are spread by the bite of the Anopheles mosquito and occasionally by blood or blood-contaminated needles. Both the human liver and red blood cells and the salivary gland of the mosquito are required for completion of the life cycle of this pathogen.

Screen for Therapeutic Agents

Another human parasite, *Fasciola hepatica* or the human liver fluke, has a complex life cycle, requiring water snails as intermediate hosts. Humans and other mammals acquire the organism by eating cyst-contaminated water plants. The cysts release immature flukes that migrate to the liver and gallbladder. A high load of the parasite may obstruct the biliary tract. Other similar parasites that can involve humans, such as *Clonorchis sinensis* (Chinese or Oriental Liver Fluke), or *Opisthorchis felineus* and *Opisthorchiasis viverrini* (Cat Liver Fluke) May also be studied by infecting the chimeric hosts of the invention.

Various drugs may be administered to the host to combat pathogen infections, and the effect on hepatocytes can be determined by invasive or non-invasive techniques. Non-invasive techniques include NMR, CAT scans, fluoroscopy, roentgenography, radionucleotide scanning, ultrasonography, electrocardiography, electroencephalography, evoked potentials, etc. Invasive techniques include biopsy, autopsy, laparotomy, intermittent intravenous blood sampling, or intravenous catheterization, etc. Convenient placement of various devices, e.g., catheters, electrodes, etc. may be performed for continuous monitoring.

Use of the chimeric animal in studying the effect of drugs on pathogenic or parasitic infection may begin with administration of the drug prior to, substantially concomitant with, and/or subsequent to the administration of the infectious dose of pathogen. Administration of the drug will usually begin not earlier than 7 days prior to infection, more usually not more than about 1 day prior to infection. In most cases, administration of the drug will begin not later than about 7 days after infection, more usually not later than about 1 day after infection. However, for studies of chronic infections, drug treatment may be started after as much as one year after infection, usually after six months, more usually after one month. After initial screening, different periods of time may be of interest in establishing the effectiveness of the drug.

The manner of administration will vary greatly, depending upon the nature of the drug. It may be provided orally, ad libitum, intraperitoneally, intravascularly, subcutaneously, intrathymic ally, or the like. Usually, different dosage levels will be employed, based on past experience with the drug, anticipated levels with human treatment, toxicity or side effects, experience with the particular chimeric host, and the like. The effect of the drug may be monitored for any convenient time, usually at least 1 week from the initiation of administration of the drug, more usually at least 2 weeks, and at times for periods as long as 6 weeks or more. Preferably, determinations will be made in the period from about 2–6 weeks.

The animals of the invention can also be used to identify and/or determine the efficacy of vaccines, i.e. therapeutic agents that have the ability to prevent or decrease the infectivity of a viral pathogen that infects human hepatocytes, e.g., the human hepatitis viruses. By providing for pathogenic infection of the xenogeneic tissue, the effect of various drugs in protecting the host tissue from the pathogen, as well as being cytotoxic to or suppressive of the pathogen in a cellular environment can be determined.

Candidate therapeutic agents can be obtained from a wide variety of sources including: libraries of synthetic or natural compounds; random and directed synthesis of organic compounds and biomolecules; including randomized oligonucleotides and oligopeptides; libraries of natural compounds (e.g. bacterial, fungal, plant and animal extracts);and natural or synthetically produced libraries and compounds. Each of these can be modified through conventional chemical, physical and biochemical means, and may be used to produce combinatorial libraries. Known pharmacological compounds may be subjected to directed or random chemical modifications, such as acylation, alkylation, esterification, amidification, etc. to produce structural analogs.

In Vivo Nucleic Acid-based Therapy

Nucleic acid-based agents that inhibit or enhance gene expression, function, or activity, including nucleotides, polypeptides, and other molecules such as antisense oligonucleotides and ribozymes, and dominant negative mutants targeted at genes involved in viral infection, e.g., hepatitis infection, liver regeneration, and the like. These therapeutics can be administered to the animals of the present invention to determine their efficacy in treating and/or preventing human liver infection and disease.

Expression vectors may be used to introduce a desired polypeptide-encoding gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid, retrovirus, adenovirus, and the like, where the vectors are able to transiently or stably be maintained in the cells, usually for a period of at least about one day, more usually for a period of at least about several days to several weeks.

The therapeutic nucleic acid construct may be introduced into tissues or host cells by any number of routes, including, but not necessarily limited to, viral infection, direct injection, microinjection, or fusion of vesicles. Direct injection of DNA for expression is described in, for example, U.S. Pat. No. 5,580,859. Jet injection may also be used for intramuscular administration, as described by Furth et al. (1992) Anal. Biochem. 205:365–368. The DNA may be coated onto gold microparticles, and delivered intradermally by a particle bombardment device, or "gene gun" as described in the literature (see, for example, Tang et al. (1992) Nature 356:152–154), where gold microprojectiles are coated with the PDE5A2 or PDE5A3 DNA, then bombarded into skin cells. Use of liposomes for delivery of DNA into a living cell is also known in the art, see, e.g., U.S. Pat. No. 4,394,448.

Dominant-negative forms of proteins that effectively displace or compete with native proteins, e.g., proteins that enhance or exacerbate viral infection, can be used to increase or decrease activity levels. Reagents that inhibit or enhance the expression of endogenous genes are also useful.

Antisense molecules can be used to down-regulate expression of a gene. The antisense reagent may be an oligonucleotide, particularly a synthetic oligonucleotide having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g., by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) Nature Biotechnol. 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model.

A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl. Biochem. Biotechnol.* 54:43–56.

Targeting of the therapeutic reagent to specific tissues is desirable to increase the efficiency of delivery. The targeting can be achieved by passive mechanisms via the route of administration. Active targeting to specific tissues can also be employed. The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycoplipids, polynucleotides, or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

Study of Chemically- or Physically-induced Liver Damage

Optimal management of chronic liver disease requires an understanding of factors or conditions initiating and sustaining tissue damage. Injury may derive initially from multiple physical and/or chemical sources, including: toxin or xenobiotic exposure (e.g., isoniazid, carbon tetrachloride, and ethanol); inborn errors of metabolism; and pathological accumulations of transition metals (iron or copper), endotoxins or membranocytolytic bile acids. Cells and mediators associated with inflammation, pathological expression of major histocompatibility foci on hepatocytes and biliary epithelia, aberrant initiation of apoptosis, modification of the extracellular matrix, and depletion of natural antioxidants can each play pivotal roles in the progression of the disease state. The chimeric hosts of the present invention allow the study of chronic human liver disease using an animal model that can be exposed to various systematic chemical exposures and/or physical obstructions or manipulations. For example, the long term outcome of drug related human liver disease can be examined in the animal by administering a drug over a substantial period of time and studying drug induced hepatotoxicity.

The chimeric host may also be used to determine chemicals or physical manipulations (so-called "protectants") that protect an animal from toxicity or liver damage. Therapeutic agents can be tested for their ablity to decrease or eliminate carcinogenic effects of various toxic compounds, the effect on growth and viability of hepatic tissue following exposure to toxic compounds, and the effect of combinations of compounds in decreasing negative effects of the compounds administered alone.

Study of Other Cellular Responses to Viral Infections

The host animal into which the human hepatocytes are introduced can be selected to allow the study of other cellular responses to viral infection, e.g. the immune response to infection with a hepatitis virus. For example, SCID mice with human immune systems, such as the SCID-hu mice of U.S. Pat. No. 5,811,635, can be used as the host into which the human hepatocytes are injected or transplanted. Such mice can be produced by implantation of scid/scid mice with human fetal liver, hematopoietic cells, human fetal thymus and human fetal lymph node. See McCune et al., *Science*, 241:1632–1639 (1988), wherein a chimeric mouse was created by implanting human fetal liver hematopoietic cells, fetal thymus and fetal lymph node into SCID mice to create a chimeric mouse capable of responding to vaccines with both murine and human cellular immune response and humoral immune response. Such animals can be used to determine the response of a human immune system to infection of liver cells with pathogens that infect human livers.

Study of Human Liver Development

The animals of the invention can also be used to study human liver development and function, both normal and abnormal, e.g., malignant or genetically altered. Malignant human hepatocytes can be introduced and maintained in the animal models, allowing the study of oncogenesis of the cells in an in vivo system. The development and function of normal human hepatocytes can also be studied, and may have implications for treatment of various liver dysfunctions, diseases and disorders.

For example, studies in the developing liver suggest that surrounding mesoderm and ectoderm participate in the hepatic specification of the endoderm, and that transcription factors such as cJun, retinoblastoma gene, and nuclear factor kappa B are important regulators of liver embryogenesis. Changes in different factors in liver development provides insight on the ability of the liver to respond to injury and on the molecular basis of hepatobiliary diseases. J. A. Bezerra *Semin Liver Dis.* 18:203–16 (1998). Thus, study of human hepatocyte development in the animals of the invention may have implications for abnormal as well as abnormal functions.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

The first studies were geared at finding a suitable location to maintain the human hepatocytes in the host animal. The region under the kidney capsule, portal vein and subcutaneous space on the dorsal surface of NOD/scid mice were tested as potential sites for human hepatocyte transplantation (FIG. 1). Previous studies have shown that different strains of mice were tested for their ability to maintain hepatoyctes after intraportal, subcutaneous, or intra-renal capsule transplantation. The greatest persistence were observed in NOD/scid mice, and these mice were subsequently used in the present studies, although other mice (including NIH3) can be used with the described methods.

Human hepatocytes were isolated from various donors (all HBV, HCV and HIV negative) by routine collagenase perfusion and low-speed centrifugation. The hepatocytes used for transplantation under the kidney capsule or in the subcutaneous space were mixed with MATRIGEL™ (Becton-Dickinson) prior to transplantation. The viability and maintenance of the transplanted hepatocytes in vivo were determined by periodic measurement of a hepatocyte specific, human serum marker alpha-1-antitrypsin (hAAT), as has been previously used for transplanted transgenic mouse hepatocytes that express this human transgene. K. P. Ponder et al., *Proc Natl Acad Sci USA* 88:1217–21(1991).

Human hepatocytes were transplanted into the subcutaneous space, renal capsule or into the liver by intraportal infusion. For the portal vein transplantation study, the harvested hepatocytes were resuspended in cold Williams-E Medium without serum and intraportally injected with 0.3 ml of fluid containing $2\times10^6$ hepatocytes. For the kidney capsule and subcutaneous transplantations, the hepatocytes were resuspended in cold media described above with an equal volume of cold liquid MATRIGEL™. A total of $4\times10^6$ of hepatocytes in 0.4 ml of the suspension were transplanted by dividing the dose into each kidney capsule space, and $6\times10^6$ of the hepatocytes in 0.6 ml of the suspension were transplanted in subcutaneous space between the scapulae. Because MATRIGEL™ quickly polymerizes into a three-dimensional gel at regular room temperature, all the procedures involving MATRIGEL™ were performed at 4° C. The data are a combined set of three different experiments using different adult hepatocyte donors. The viability of hepatocytes were 90%, 75% and 55% by trypan blue exclusion, and 90%, 60% and 40% by plating efficiency, respectively. Periodic serum was collected and assayed for the serum marker hAAT protein as a measure of hepatocyte survival using the ELISA protocol of K. P. Ponder et al., (*Proc Natl Acad Sci USA* 88:1217–21 (1991)). Because of the differences in viability of each liver isolate, the relative level of hAAT was compared with the value obtained 3 days after transplantation. The values represent the average relative concentration with the standard deviation. The day 3 hAAT concentrations ranged from 500 to 10,000 ng/ml.

The human hepatocytes delivered by intraportal infusion were rapidly lost (greater than a two log drop) over a period of a week, while in contrast, the subcutaneous and intra-renal transplanted hepatocytes displayed a slower decline, maintaining a small amount of human hepatocyte activity over a period of three to six months, particularly those in the kidney capsule (FIG. 1). Because the kidney capsule transplants seemed to have the longest period of survival, this method of implantation was used in further studies.

Example 2

Figure 2:
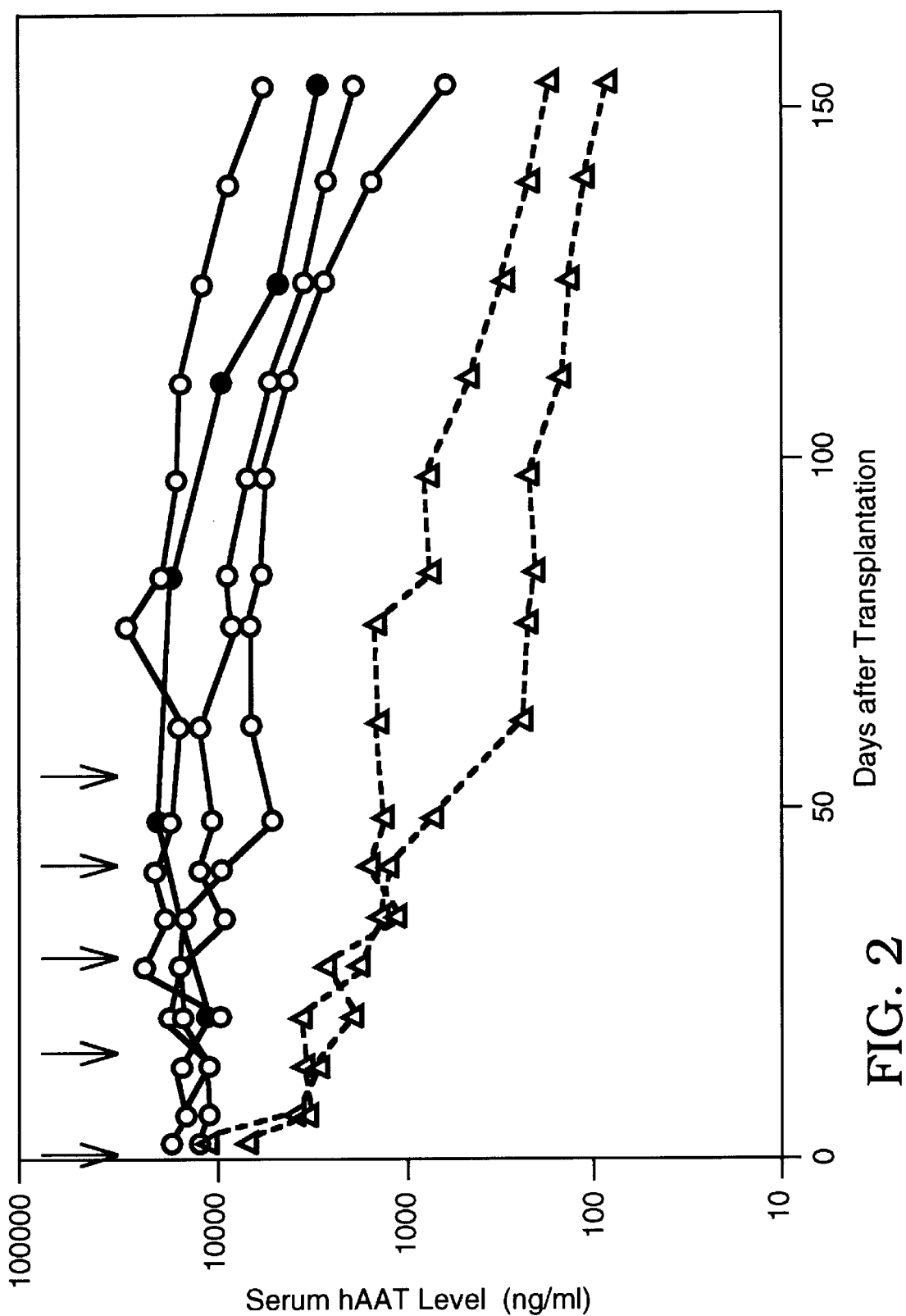
FIGS. 2 and 3 are graphs illustrating stabilization of the xenotransplants in NOD/SCID mice with cMet agonistic antibody. All the mice were transplanted with human hepatocytes under the kidney capsule at day 0 and a subset of mice (circles, filled circles represents the mouse used in FIG. 4 for HBV infection) received c-Met at days 1, 15, 29, 43, 57 (arrows) while the controls did not receive c-Met (triangles).
Figure 3:
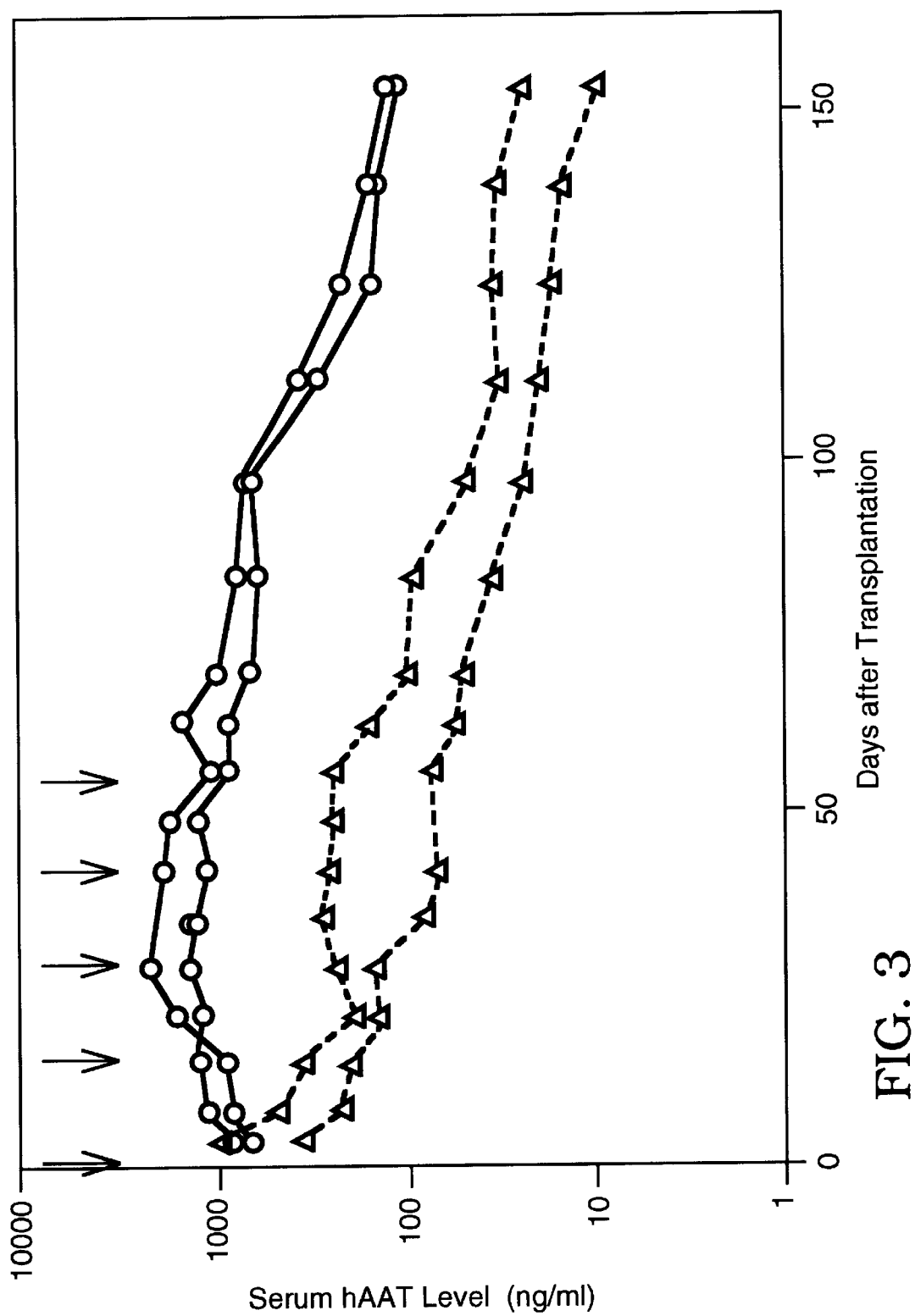

Experiments to determine the cause of the loss of human hepatocyte function were then undertaken. One testable theory is that the loss was due at least in part to the absence of an essential factor such as human hepatocyte growth factor (HGF). Because HGF has a half-life on the order of minutes, an agonistic anti-human c-Met murine IgG1 antibody was used in combination with the transplantation procedure. Fifty micrograms of the c-Met antibody was administered every 2 weeks for the first 57 days levels of hepatocyte stabilization of hAAT expression with or without c-Met were determined, as shown in FIGS. 2 and 3. FIGS. 2 and 3 represent two separate experiments with the same parameters.

All the mice were transplanted with human hepatocytes and MATRIGEL™ at day 0, and a subset of mice received c-Met at days 1, 15, 29, 43, 57; controls did not receive c-Met. The absolute concentrations of hAAT between the two experiments result from the variability in the quality of liver tissue at the time of hepatocyte isolation. The two to five fold reduction in hAAT levels observed at 5 months may have been due to the lack of c-Met administration after day 57. Nevertheless, c-Met did stabilize hepatocytes as determined by steady-state serum hAAT concentrations.

To further establish that the hepatocytes within the transplant were viable, histological analyses were performed. Representative mice were sacrificed at weeks 3 and 24 post transplantation for histological analysis. Kidney sections were taken and stained for hematoxylin and eosin staining and hAAT. Cells having the characteristic hepatocyte morphology were visible and their identity as human hepatocytes were confirmed by immunostaining for hAAT.

Example 3

Figure 4:
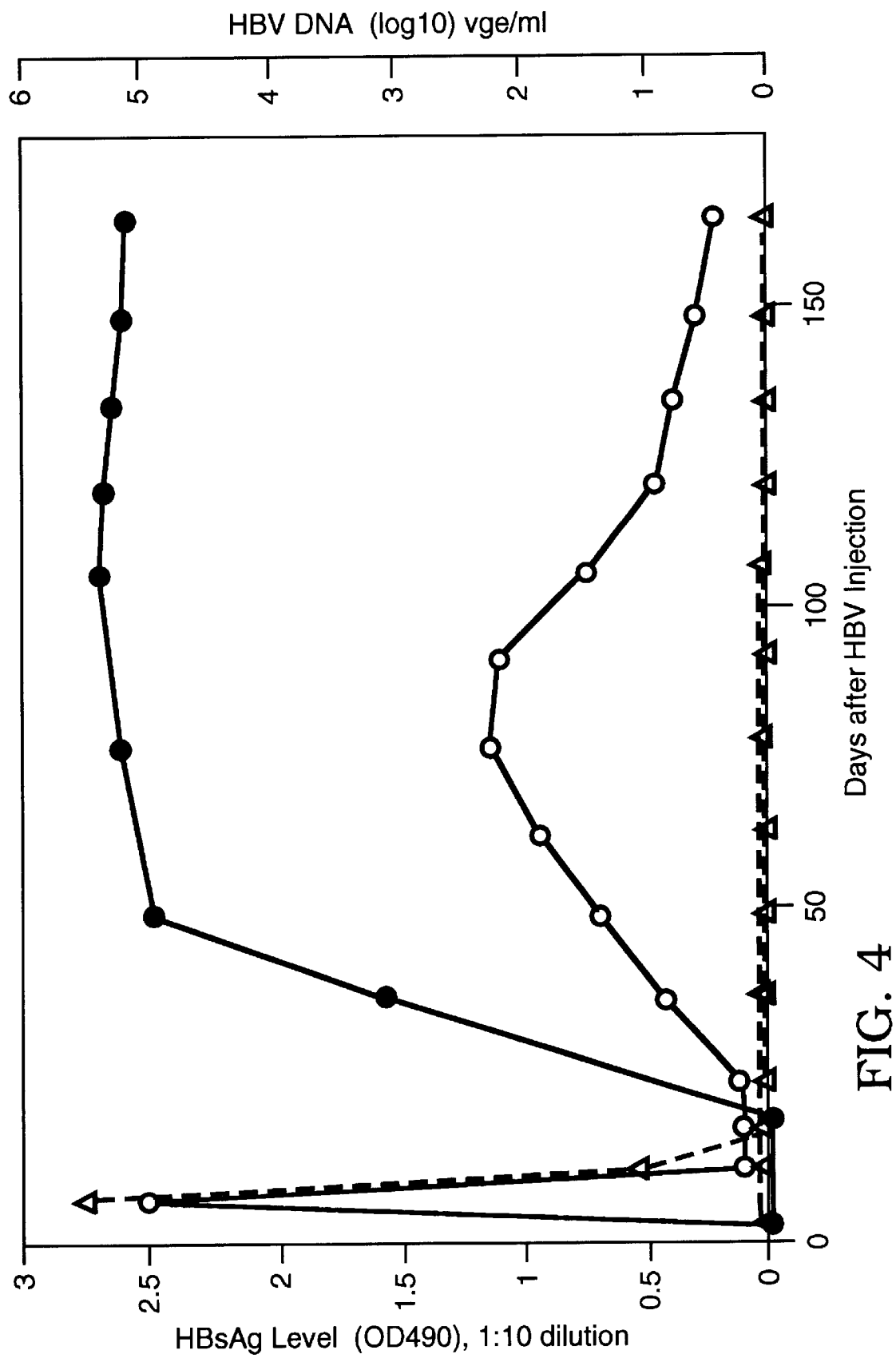
FIGS. 4 and 5 illustrate the HBV infection in chimeric mice mice. The panels A and B represent two separate experiments. Control animals received HBV but no hepatocytes (triangles). The circles and squares represent the mice that received hepatocytes and HBV. The filled symbols represent the values for serum HBV DNA titer. The open symbols represent the values for the serum HBsAg concentrations.
Figure 5:
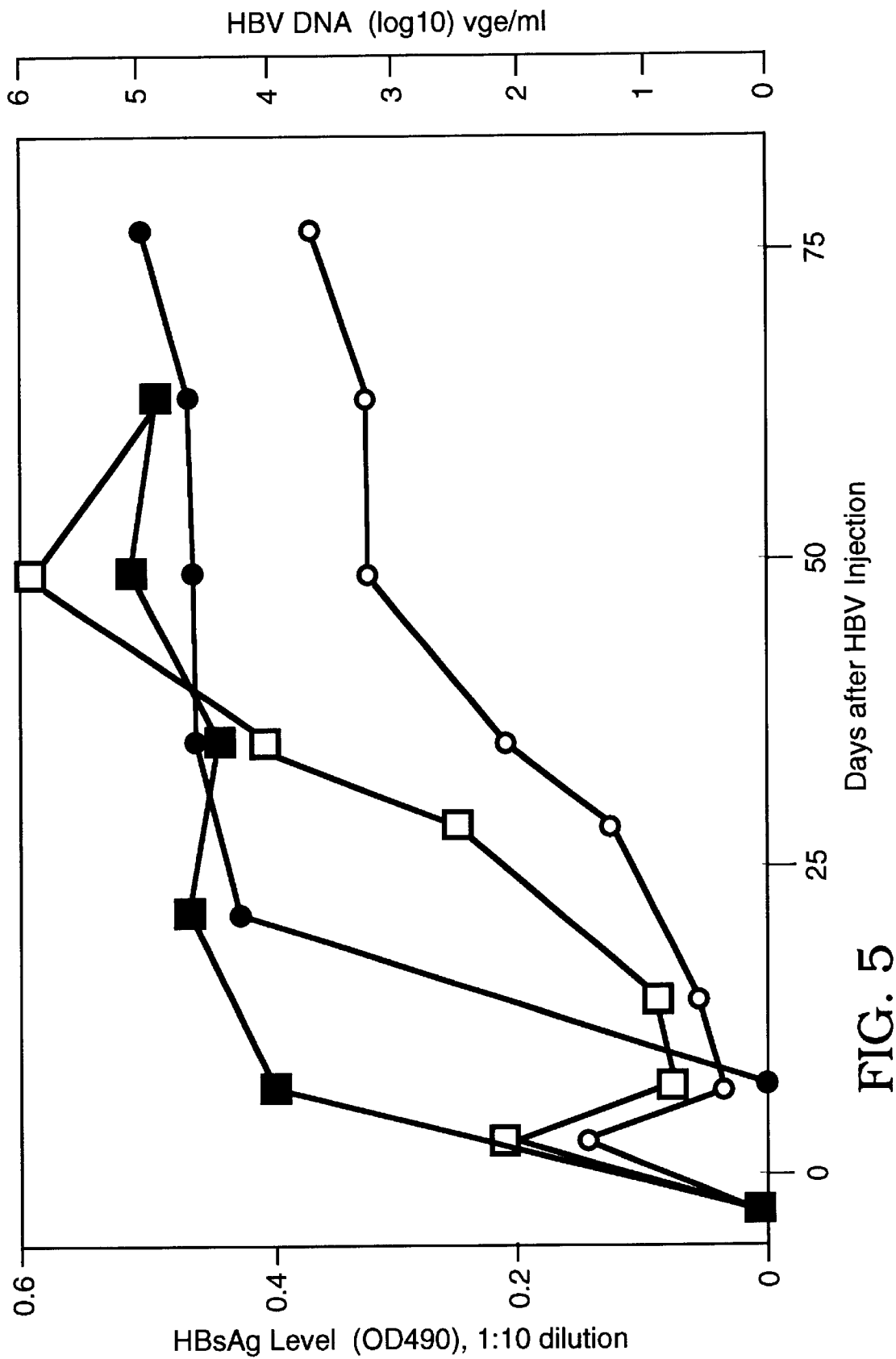

In order to establish whether or not the transplanted hepatocytes could serve as an in vivo model for infection with human hepatitis viruses, three animals that received human hepatocytes in the kidney capsule were infused 3 days later with 0.25 to $1.4\times10e^8$ HBV DNA equivalents by injection into the transplant and intravenously. Serum samples were periodically monitored for HBsAg and HBV DNA titers (FIGS. 4 and 5, respectively).

Mice were transplanted with human hepatocytes at day-3 and c-Met antibody was administered at day-2 and then on the same schedule as the experiment of Example 2. Control animals received no hepatocytes. Mice were either inoculated with 250 µl of HBV infected single human serum containing $2.5\times10^7$ HBV DNA equivalents or 250 µl of pooled donor sera containing $1.4\times10^8$ HBV DNA equivalents in a split dose administered via the kidney capsule and intravenously. The later two mice were transplanted with hepatocytes that were cultured for 48 hours prior to transplantation. The original viability of the hepatocytes used in the first mouse was 90% by trypan blue exclusion and plating efficiency, and in the second set of animals 85%o and 55% by trypan blue exclusion and plating efficiency, respectively.

HBV DNA quantification was by a quantitative HBV DNA PCR ELISA. Briefly, mouse serum was diluted in PBS containing 10% fetal bovine serum and denatured with an equal volume of 0.2N sodium hydroxide. After incubation at 60° C., the mixture was neutralized and added to a PCR master mix containing buffer, 2.5 mM magnesium chloride, 200 mM dNTP, 2.5 units Taq DNA polymerase (Life Technologies, Gaithersburg, Md.), and 30 pmol each of primers HBV-1 (GGAGTGTGGATTCGCACT; SEQ ID NO:1) and biotinylated HBV-2 (TGAGATCTTCTG CGACGC; SEQ ID NO:2) (Erhardt et al, J. Clin. Microbiol. 34:1885–1891 (1996)). Serial 0.5 log dilutions of hepatitis B genome-containing plasmid were amplified in parallel, along with in-house prepared mouse serum standards. The PCR product was then quantified using binding to avidin-coated plates, then probing with a digoxigenin-labeled HBV oligonucleotide (HBV-3: TAGAAGAAGAACTC-CCTCGCCTCGCAGACG; SEQ ID NO:3) which was detected by a peroxidase-labeled anti-DIG antibody (Boehringer-Mannheim) reacted with appropriate substrate. ODs were read against a curve generated using known amounts of HBV DNA. The assay has proven to give results equivalent to those using the Roche Amplicor system. The mean variability ranges from 1.5 fold in a the same assay to 1.8 fold in samples tested in different assays.

The transient first peak of HBsAg was present between days 3–7 in control non-human hepatocyte containing animals because of the injected material. However, the amount of HBsAg and HBV DNA titers slowly increased starting at about 2 weeks in mice transplanted with human hepatocytes and c-Met antibody and persisted for at least 5 months. The peak HBV titers ranged from 1.5 to $2.2 \times 10^5$ DNA particles per ml in different animals. There was an eventual decrease in HBsAg and half log drop in HBV DNA titers 4 months after infusion which may have been due to the lack of anti-cMet antibody. The rise in HBsAg and HBV DNA were not observed in non-transplanted animals infused with HBV. Because of the nature of the cells within the explant, it is unlikely that enough DNA can be isolated to establish the molecular forms of the HBV genomes in vivo.

Example 4

To further establish the presence of HBV production, the implanted hepatocytes within the renal capsule at 24 weeks post-infection (a time when the titer had fallen by 5-fold) were examined by immunohistochemical staining and found that it contained HBcAg in the cytoplasm in more than half of the cells and occasionally in the nucleus. Immunohistochemical staining for hepatitis B viral antigens was performed on formalin-fixed, paraffin embedded sections of liver and kidney. A polyclonal rabbit anti-HBcAb (Cortex Biochem, San Leandro, Calif., 94577) from animals immunized with recombinant HBcAb was used as a primary antibody at a 1:200 dilution. Primary antibody binding was detected using a Supersensitive Streptavidin peroxidase kit (BioGenex, San Ramon, Calif.) with goat anti-rabbit antibody following manufacturers directions with AEC as the chromagen. For detection of HBsAg a polyclonal rabbit antibody conjugated to biotin (Cortex Biochem, San Leandro, Calif.) was used at a 1:200 dilution. Streptavidin peroxidase (BioGenex, San Ramon, Calif.) was applied to detect bound primary antibody. Methyl green pyronin was used as a counter stain. HBV-infected human liver was used as positive control tissue. Liver and kidney from an uninfected mouse that had been implanted with human hepatocytes served as a negative control.

HBsAg was not as abundant as HBcAg. No HBsAg or HBcAg staining was detected in the mouse kidney or liver. There was no staining apparent in the implanted hepatocytes in an animal that did not receive hepatitis B virus injection. This model demonstrates that human hepatocytes can be engrafted long-term in mice and serve as a model for a human diseases such as hepatitis B virus infection. This model will allow further studies on the process of viral infection and may allow for important advances in developing additional models of human liver disease.

Example 5

Mice having transplanted human hepatocytes were also tested for their ability to be co-infected with HBV and HDV. Two mice were inoculated with HBV and injected 60 days later with HDV-positive serum obtained from an infected chimpanzee. HDV genomic RNA became detectable in the serum by day 10 and remained so through at least 4 weeks after inoculation. The RNA was the result of an established infection, and not simply residual inoculum, as HDV RNA was undetectable at day 2. In addition, no HDV RNA could be detected at corresponding times in control mice that received HBV and HDV without prior hepatocyte transplantation, mice that received hepatocytes and HBV but no HDV, or mice that received hepatocytes but no HBV or HDV.

To confirm that the HDV RNAs detected in the serum reflected infection of the transplanted hepatocytes, immunohistochemistry was performed on liver tissue sections with an antibody against hepatitis delta antigen. Serial sections showed co-localization of HBcAg and a strong nuclear staining pattern for HDAg, a pattern that is characteristic of HDV infection. This staining pattern was readily apparent among the transplanted human hepatocytes from mice inoculated with HBV and HDV, but not in any of the other control mice.

In the xenotransplantation mouse model of the invention, HBV infection occurs by infusion of the virus in vivo. The ability to infect these mice directly with HBV represents a more biologically relevant system. The transplanted human hepatocytes are not only susceptible to HBV and HDV infection, but they are also able to support the replication and release of these viruses back into the serum. Thus, these essential aspects of the HDV life cycle are now be amenable to study in our small-animal model. This model provides an excellent system in which to test proposed new antiviral strategies directed against HDV.

Example 6

The effect of neovascularization on xenotransplantion was examined by pretreatment of the transplantation site with an angiogenic factor. The ability of pre-treatment with an angiogenic factor to induce prolonged survival of the ectopically transplanted hepatocytes was examined for subcutaneous transplantation. In particular, the ability of acidic fibroblast growth factor (aFGF), to induce prolonged survival of subcutaneous transplants was studied.

First, the ability of aFGF to recruit subcutaneous vasculature was tested using micospheres containing different doses of aFGF. The microspheres were prepared using polylactic co-glycolic acid and polyethylene glycol by a double-emulsion technique, and the resulting mean diameter of these microspheres was 10 μM as measured by a Coulter multisizer. Heparin was also encapsulated in the microspheres in order to stabilize the aFGF. The microspheres were then tested for the ability to increase vascularization in wild-type mice.

Different dosages of aFGF tested for vascular recruitment were used as follows: Group 1 microspheres, which were composed of saline plus heparin; Group 2 microspheres, which were composed of aFGF and heparin with a release rate of 0.167 ng of aFGF/day; and Group 3 microspheres which were composed of aFGF and heparin with a release rate of 1.67 ng of aFGF/day. The microspheres of each group were resuspended in cold Williams medium E with an equal volume of MATRIGEL™ and incubated at 4° C. overnight. Each group of resuspended microspheres was injected into the subcutaneous space on the back of FVB/N test mice (n=2/group). The injected microsphere solutions were found to form a gel soon after injection.

All mice were sacrificed at day 10 and subcutaneous tissues were excised and fixed in 10% formalin. These tissues were histologically examined by H&E sections for the evaluation of the recruitment of vasculature within or surrounding area of the gel. Mice injected with the Group 1 microspheres did not show any increase in vascularization at the site of injection, as very few infiltrated or migrated blood cells were detected. In contrast, a significant number of small vessels were seen surrounding area of injection of Group 2 mice, and vascular-like structures were formed within the injected gel. The mice injected with the Group 3 microspheres exhibited a slight increase of the vessel numbers in the area surrounding the injection, but the effect was not as dramatic as that seen for the mice injected with Group 2 microsomes, and no vascular-like structures were observed within the injected gel.

The ability to induce neovascularization at a subcutaneous site by aFGF then used to test whether this effect could increase survival of subcutaneous hepatocyte xenotransplants. Hepatocytes were isolated from two transgenic mouse livers expressing the marker human alpha 1-antytrypsin (hAAT) using modified two-step collagenase perfusion method, where liver was perfused in situ through the inferior vena cava. This mouse line had been created in FVB/N mouse by microinjecting an hAAT cassette including 12.8 kb of hAAT gene down stream from the liver specific hAAT promoter. Hepatocytes were purified (greater than 98%) by three rounds of low-speed centrifugation. The viability of the isolated hepatocytes were measured by trypan blue exclusion test. The freshly isolated mouse hepatocytes were resuspended in cold William's medium E with an equal volume of MATRIGEL™ ($1 \times 10^7$ cells/ml). Different amounts of aFGF were also mixed in the medium for each group of microsomes: the medium for Group 1 microsomes contained vehicle alone (saline), the medium for Group 2 microsomes contained 1 ng/ml aFGF, and the medium for Group3 microsomes contained 10 ng/ml aFGF.

Syngeneic FVB/N mice (non-transgenic; n=2 in each group) were used as the transplantation recipients. The three different microsphere groups (Groups 1 to 3) were introduced to the subcutaneous space of the syngeneic mice 8 days prior to hepatocyte transplantation. After the 8 day period, approximately $1 \times 10^7$ isolated hepatocytes were transplanted at the site of each microsphere injection using a 21-G needle.

The survival of the transplanted hAAT transgenic mouse hepatocytes was monitored by periodical measurement of serum hAAT in the recipients using the ELISA protocol of K. P. Ponder et al., (*Proc Natl Acad Sci USA* 88:1217–21 (1991)). Mice were sacrificed at 5 weeks after transplantation, and the transplants histologically evaluated.

Figure 6:
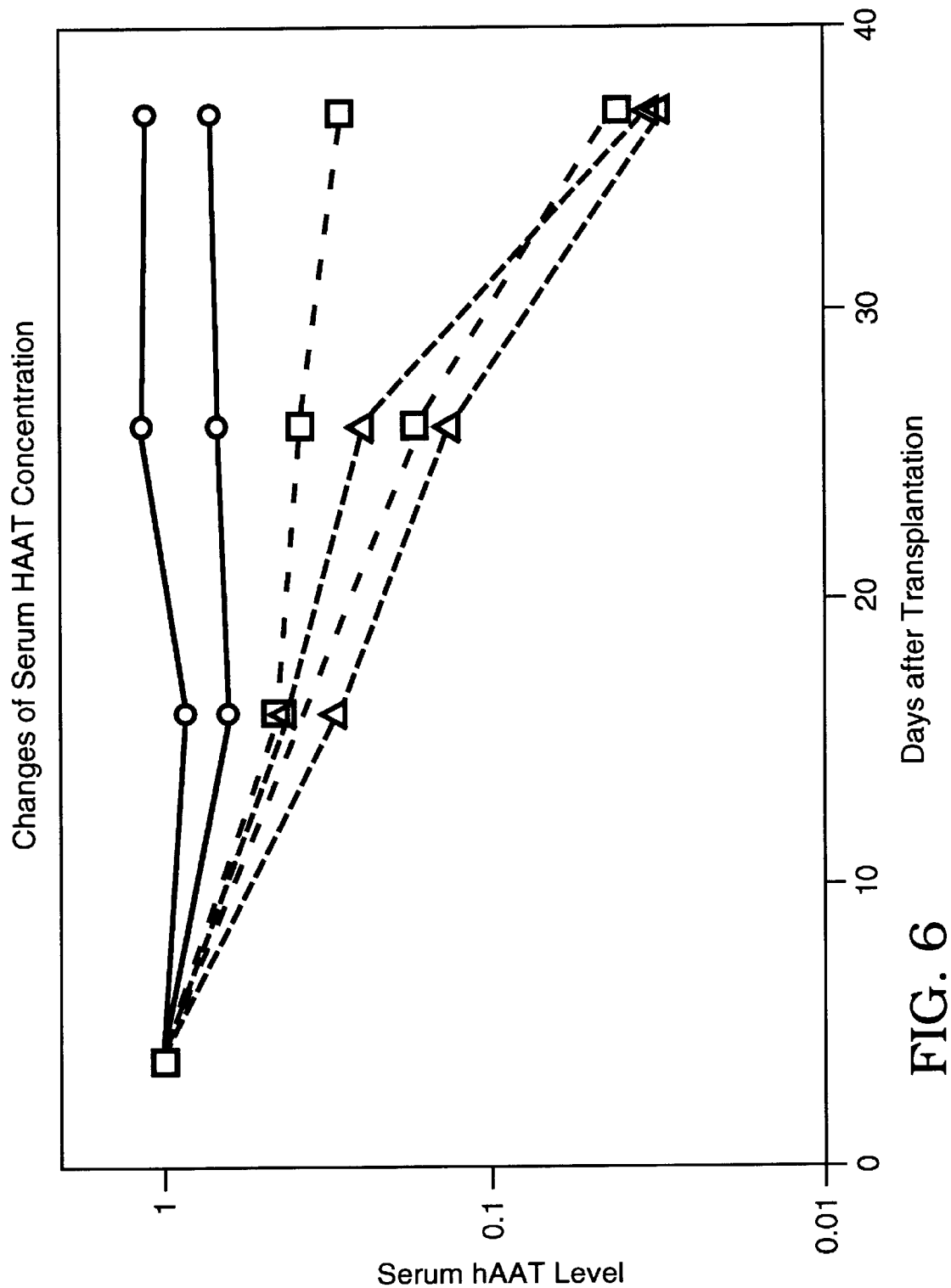
FIG. 6 is a graph illustrating survival of the transplanted hAAT transgenic mouse hepatocytes at varying FGF concentrations. Control animals received microspheres without aFGF (squares). The animals receiving microsomes with an aFGF release rate of 0.167 ng/day are denoted by circles, and animals receiving microsomes with an aFGF release rate of 1.67 ng/day are denoted by a triangle. Experiments were performed in duplicate.

The transgenic mouse hepatocytes in mice injected with microsome Groups 1 and 3 were rapidly lost over a period of 5 weeks (FIG. 6). In contrast, the survival of the transplanted hepatocytes in mice injected with Group 2 microsomes persisted during the experimental period. Histological determination was performed to determine whether vessel formation occurred within the transplants in the three groups. In mice injected with microsomes of Groups 1 and 3, vascular-like structures were rarely seen within the transplants. In contrast, many small vessels were observed within the transplants of mice injected with Group 2 microsomes. Most importantly, red blood cells were detected in vessels of mice injected with Group 2 microsomes, which is a indicative of functional vessels.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An immunocompromised mouse comprising:
engrafted functional human hepatocytes, wherein an activator of human hepatocyte growth factor receptor is administered to the mouse, wherein the human hepatocytes are maintained in the mouse for at least five months.

2. The mouse of claim 1, wherein said human hepatocyte growth factor receptor activator is administered by dosage at regular intervals following transplantation.

3. The mouse of claim 1, wherein said human hepatocyte growth factor receptor activator is administered continuously following transplantation.

4. The mouse of claim 1, wherein said mouse further comprises an agent that promotes the colonization and growth of human hepatocytes in said host.

5. The mouse of claim 1, wherein said human hepatocyte growth factor receptor activator is selected from the group consisting of: human hepatocyte growth factor, human hepatocyte growth factor receptor, a constitutively activated human hepatocyte growth factor receptor, and a small molecule that activates human hepatocyte growth factor receptor.

6. The mouse of claim 1, wherein factors other than the human hepatocyte growth factor receptor are administered to said mouse.

7. The mouse of claim 6, wherein an angiogenic factor is administered to said host prior to transplantation.

8. The mouse of claim 1, wherein a partial hepatectomy to the host is performed prior to introduction of said human hepatocytes.

9. The mouse of claim 1, wherein the mouse is homozygous for a mutation at the scid locus.

10. A method for producing a chimeric mouse comprising engrafted functional human hepatocytes, said method comprising:
introducing human hepatocytes into an immunocompromised mouse, wherein an activator of human hepatocyte growth factor receptor, is administered to said mouse in an amount sufficient to allow engraftment of said human hepatocytes; and,
said human hepatocytes are maintained in the mouse for at least five months.

11. The method of claim 10, wherein said method further comprises introducing into said mouse an agent that promotes the colonization and growth of human hepatocytes in said mouse.

12. The method of claim 10, wherein the human hepatocytes are introduced under the kidney capsule.

13. The method of claim 10, wherein the human hepatocytes are introduced at a subcutaneous site.

14. The method of claim 10, the method further comprising:
treating a transplantation site with an angiogenic factor; wherein said human hepatocytes are introduced to the treated transplantation site.

15. The method of claim 10, further comprising performing a partial hepatectomy to the host prior to the introduction of human hepatocytes.

16. An immunocompromised mouse comprising:
engrafted functional human hepatocytes, wherein a protein activator of human hepatocyte growth factor receptor is administered to said mouse, such that the human hepatocytes are maintained in the mouse for at least five months.

17. The host of claim 16, wherein the mouse is homozygous for a mutation at the scid locus.

18. The mouse of claim 16, wherein said human hepatocyte growth factor receptor activator is administered by dosage at regular intervals following transplantation.

19. The mouse of claim 16, wherein said human human hepatocyte growth factor receptor activator is administered continuously following transplantation.

20. The mouse of claim 16, wherein said human hepatocyte growth factor receptor activator is an antibody that specifically binds human c-Met.

21. The mouse of claim 20, wherein the antibody specifically binds to an epitope on the extracellular domain of human hepatocyte growth factor receptor.

22. The mouse of claim 16, wherein said human hepatocyte growth factor receptor activator is selected from the group consisting of: human hepatocyte growth factor, human hepatocyte growth factor receptor, and a constitutively activated human hepatocyte growth factor receptor.

23. The mouse of claim 16, wherein an angiogenic factor is administered to said mouse prior to transplantation.

24. The mouse of claim 18, wherein a partial hepatectomy to the host is performed prior to introduction of human hepatocytes.

25. A method for producing a chimeric mouse comprising engrafted functional human hepatocytes, said method comprising:

introducing human hepatocytes into an immunocompromised mouse, wherein a protein activator of human hepatocyte growth factor receptor is administered to said mouse in an amount sufficient to allow engraftment of said human hepatocytes; and, said human hepatocytes are maintained in the mouse for at least five months.

26. The method of claim 25, wherein the human hepatocytes are introduced under the kidney capsule.

27. The method of claim 25, wherein the human hepatocytes are introduced at a subcutaneous site.

28. The method of claim 25, the method further comprising:

treating a transplantation site with an angiogenic factor; wherein said human hepatocytes are introduced to the treated transplantation site.

29. The method of claim 24, further comprising performing a partial hepatectomy to the mouse prior to the introduction of human hepatocytes.

30. The method of claim 25, wherein said human hepatocyte growth factor receptor activator is an antibody directed against the extracellular domain of c-Met.

\* \* \* \* \*

UNITED STATES PATENT AND TRADEMARK OFFICE
CERTIFICATE OF CORRECTION

PATENT NO. : 6,660,905 B1
DATED : December 9, 2003
INVENTOR(S) : Kay, Mark A. et al.

It is certified that error appears in the above-identified patent and that said Letters Patent is hereby corrected as shown below:

<u>Title page,</u>
Item [54], Title, should read -- ANIMALS COMPRISING HUMAN HEPATOCELLULAR TISSUE --

Signed and Sealed this

Twenty-eighth Day of June, 2005

JON W. DUDAS
*Director of the United States Patent and Trademark Office*